United States Patent [19]

Deasy et al.

[11] Patent Number: 5,418,827
[45] Date of Patent: May 23, 1995

[54] METHOD FOR RADIATION THERAPY PLANNING

[75] Inventors: Joseph O. Deasy, Middleton; Renato De Leone, Madison, both of Wis.

[73] Assignee: Wisconsin Alumino Research Foundation, Madison, Wis.

[21] Appl. No.: 79,026

[22] Filed: Jun. 18, 1993

[51] Int. Cl.⁶ ............................................. A61N 5/01
[52] U.S. Cl. .................................... 378/65; 378/153; 364/413.26
[58] Field of Search ................. 364/413.26; 250/492.1; 378/64, 65, 68, 69, 153

[56] References Cited

U.S. PATENT DOCUMENTS

| | | | |
|---|---|---|---|
| 3,487,559 | 1/1970 | Freedman | 434/218 |
| 3,987,281 | 10/1976 | Hodes | 364/413.26 |
| 4,754,147 | 6/1988 | Maughan et al. | 250/505.1 |
| 4,794,629 | 12/1988 | Pastyr et al. | 378/152 |
| 4,817,125 | 3/1989 | Sklebitz | 378/152 |
| 4,868,843 | 9/1989 | Nunan | 378/152 |
| 4,868,844 | 9/1989 | Nunan | 378/152 |
| 4,905,268 | 2/1990 | Mattson et al. | 378/158 |
| 4,987,309 | 1/1991 | Klasen et al. | 250/492.1 |
| 5,012,506 | 4/1991 | Span et al. | 378/152 |
| 5,317,616 | 5/1994 | Swerdloff et al. | 378/65 |
| 5,351,280 | 9/1994 | Swerdloff et al. | 378/65 |

FOREIGN PATENT DOCUMENTS

| | | |
|---|---|---|
| 0480035A1 | 4/1992 | European Pat. Off. . |
| 0556874A2 | 8/1993 | European Pat. Off. . |
| WO90/14129 | 11/1990 | WIPO . |
| WO90/14861 | 12/1990 | WIPO . |
| WO91/18552 | 12/1991 | WIPO . |

OTHER PUBLICATIONS

Calculation and Application of Point Spread Functions for Treatment planning with High Energy Photon Beams, *Acta Oncologica* 26 (1987) pp. 49–56, A. Ahnesjo, et al.
Methods of Image Reconstruction from Projections Applied to Conformation Radiotherapy, *Phys. Med. Biol.*, 1990, vol. 35, No. 10, 1423–1434, Bortfeld et al.
Feasibility Solutions in Radiation Therapy Treatment Planning, *Dept. of Radiation Therapy*, Univ. of PA School of Med., pp. 220–224, Altschuler, et al. (1984).
A Primer on Theory & Operation of Linear Accelerators in Radiation Therapy, *Medical Physics Pub. Corp.*, (1981) C. J. Karzmark, et al.
The Accuray Neutron 1000, A Medical Systems for Frameless Stereotoxic Radiosurgery, Accuray, Inc., J. R. Adler, et al., May 1992.
Optimization of Stationary and Moving Beam Radiation Therapy Techniques, *Radiotherapy and Ocology*, 12 (1988) 129–140, A. Brahme.
A Unified Approach to the Optimization of Brachytherapy and External Beam Dosimetry, *Int. J. Radiation Ocology Biol. Phys.*, vol. 20 pp. 859–873, Holmes, et al. (1991).
Optimization by Simulated Annealing of Three-Dimensional Conformal Treatment Planning for Radiation Fields Defined by a Multileaf Collimator, *Phys. Med. Biol.*, 1991, vol. 36, No. 9, 1201–1226, S. Webb.

(List continued on next page.)

*Primary Examiner*—Paul M. Dzierzynski
*Assistant Examiner*—David Vernon Bruce
*Attorney, Agent, or Firm*—Quarles & Brady

[57] ABSTRACT

A radiation therapy apparatus, for a radiation therapy machine providing an irradiation of a tumor at 360° about the tumor within a plane, determines a distribution of charges in a conductor that would produce a potential energy field matching the desired dose to the tumor in the plane. The fluence of any given ray through the tumor may be determined by summing the charges along the ray's path. The distribution may include areas of no irradiation which may require negative fluences. Physically realizable non-negative fluences are obtained by an iterative process of adjusting an input dose map in light of the actual dose produced by the calculated fluences.

16 Claims, 5 Drawing Sheets

OTHER PUBLICATIONS

Optimization of Conformal Radiotherapy Dose Distributions by Simulated Annealing, *Phys. Med. Biol.*, vol. 34, No. 10, 1349–1370, S. Webb (1989).

A Constrained Least-Squared Optimization Method for External Beam Radiation Therapy Treatment Planning, *Med. Phys.* 11(5), Sep./Oct. 1984 pp. 659–664, G. Starkschall.

On the Use of Cimmino's Simultaneous Projections Method for Computing a Solution of the Inverse Problem in Radiation Therapy Treatment Planning, *Inverse Problems*, 4 (1988) 607–623, Y. Censor, et al.

Tomotherapy: A New Concept for the Delivery of Conformal Radiotherapy using Dynamic Compensation, Jul. 1992, Swerdloff, et al.

Progress In Medical Radiation Physics vol. 2, 1985, edited by Colin Orton, Plenum Press, W. A. Jennings pp. 1–111.

METHOD FOR RADIATION THERAPY PLANNING

This invention was made with the United States Government support awarded by the Air Force Office of Scientific Research and the United States Government (AFOSR), Grant No. 89-0410. The United States Government has certain rights in this invention.

BACKGROUND OF THE INVENTION

1. Field of the Invention

This invention relates generally to radiation therapy equipment for the treatment of tumors, or the like, and specifically to a radiation therapy planning method for calculating the necessary beam strengths, in a therapy system for delivering multiple beams at different angles within a plane, so as to precisely regulate the dose of radiation within irregularly shaped zones within the patient.

2. Background Art

Medical equipment for radiation therapy treats tumorous tissue with high energy radiation. The dose and the placement of the dose must be accurately controlled to insure both that the tumor receives sufficient radiation to be destroyed, and that damage to the surrounding and adjacent non-tumorous tissue is minimized.

Internal-source radiation therapy places capsules of radioactive material inside the patient in proximity to the tumorous tissue. Dose and placement are accurately controlled by the physical positioning of the isotope. However, internal-source radiation therapy has the disadvantages of any surgically invasive procedure, including discomfort to the patient and risk of infection.

External-source radiation therapy uses a radiation source that is external to the patient, typically either a radioisotope, such as $^{60}Co$, or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue may be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam are changed, reducing the total dose to each such element of healthy tissue during the entire treatment.

The irradiation of healthy tissue also may be reduced by tightly collimating the radiation beam to the general cross section of the tumor taken perpendicular to the axis of the radiation beam. Numerous systems exist for producing such a circumferential collimation, some of which use multiple sliding shutters which, piecewise, may generate a radio-opaque mask of arbitrary outline.

As part of collimating the beam to the outline of the tumor, the offset angle of the radiation beam, with respect to a radius line between the radiation source and the center of rotation of the radiation source, may be adjusted to allow the treated area to be other than at the center of rotation. Simultaneously changing the offset angle and the width of the radiation beam as a function of gantry angle allows tumorous tissue having an irregular cross-section within a plane parallel to the radiation beam to be accurately targeted. The width and offset angle of the radiation beam may be controlled by the use of a multiple-leaf collimator.

Adjustment of the offset angle, center, and size of the radiation beam at various gantry angles allows considerable latitude in controlling the dose. Nevertheless, these approaches still impart a considerable amount of undesired dose to healthy tissue, especially where the tumor is concave or highly irregular.

A radiotherapy machine providing much reduced irradiation of healthy tissue is described in co-pending U.S. patent application Ser. No. 07/865,521, filed Mar. 19, 1992 and assigned to the same assignee as the present application. This radiotherapy machine has a number of radiation attenuating leaves in a rack positioned within the radiation beam before the beam enters the patient. The leaves slide into the radiation beam, in a closed state, to block a given ray of the beam, and out of the radiation beam, in an open state, to allow unobstructed passage of a given ray of the beam. By controlling the ratio of time spent in the open and closed states, each ray may be attenuated over a continuous range of intensities.

This ability to control not just the outline of the radiation but the intensity of each individual ray allows extremely precise control of the irradiation volume.

In theory, with the proper modulation of each ray of the beam as the beam revolves about the patient through a range of angles, the radiotherapy machine can precisely place the dose within even concave or highly irregular zones. Importantly, the radiation also can be accurately excluded from zones that include radiation sensitive organs or the like.

Such dose placement techniques require allocating the dose received by any volume element of the patient among the many possible rays of radiation at different gantry angles. This allocation, manifest as a set of beam intensities for each ray of the beam and for each gantry angle of the beam, is termed a treatment sinogram.

The above referenced co-pending application describes a method of producing a treatment sinogram using techniques analogous to the image reconstruction techniques of computed tomography ("CT") with the important distinction that CT image reconstruction derives an image of the patient by measuring the attenuations of a plurality of rays through the patient, whereas the radiotherapy system impresses a "dose image" on the patient by pre-attenuating a set of radiation beams at the various angles about the patient.

The sinogram generating techniques referred to above challenge the computing capability of present computer hardware.

SUMMARY OF THE INVENTION

The present invention provides a new technique for computing a treatment sinogram. The technique models the desired dose distribution within the patient as an electropotential field and employs the methods of electrostatics to allocate the contributed dose among differently angled rays. This technique may provide improved computational efficiency for the generation of a treatment sinogram for radiation therapy, and, at certain steps, lends itself to execution on a novel and extremely rapid electrostatic computer, to be described.

Specifically, an electronic computer receives data indicating the desired dose to be deposited by the multiple radiation beams of the radiation therapy machine along the slice through the volume of the patient. A charge calculator receiving this desired dose calculates the distribution of electrical charges within the slice that would produce a potential energy field corresponding to the desired dose map. An integrator simply integrates these charges along any path through the slice to determine the intensity of the ray along that path.

Thus, it is one object of the invention to provide a simple and fast method of producing a treatment sinogram from a desired dose map. Formulating the problem as one of electrostatics permits a wide variety of numerical techniques to be employed in the actual calculation, potentially providing improved performance over approaches based on computed tomography concepts. In one embodiment, the charge calculator may be a conductive sheet formed from a plurality of connectable conductive elements first joined together to receive a charge, in at least one dose region, and second separated to measure the charge on each isolated element. The integration means is a digital computer for receiving the charge values into an array and performing the necessary interpolation and integration.

Thus, it is another object of the invention to provide a method for generating a treatment sinogram that is readily adaptable to an extremely rapid analog computing device. The conductive sheet calculates the charge distribution with actual charges on an essentially instantaneous basis. Each charge computes its own position simultaneously with other charges, in a manner analogous to but far faster than a massively parallel digital computer.

The desired dose map may have at least two zones: a first tumor zone which is intended to receive at least a treatment threshold of radiation and a second organ zone which is intended to receive no more than a tolerance threshold of radiation. The charge calculator calculates the charge that would produce the potential energy field corresponding to a current dose map (initially equal to the desired dose map) in each zone and the integrator integrates along a given path through the slice to determine the ray weight along that path.

A means is provided by repeating the integration of charges to determine the weighting for many rays around different angles of the gantry to create a sinogram of fluence values and a means is provided for setting any negative fluence values in the sinogram to zero to create an adjusted sinogram. A dose calculator receiving this adjusted sinogram determines the actual dose that would be produced by this adjusted sinogram. The current dose map is modified according to the difference between the desired dose and the actual dose. In one embodiment, the current dose map is modified for the next iteration by subtracting the difference from the current dose map.

It is thus another object of the invention to permit certain zones to be assigned maximum dose limitations to protect radiation sensitive organs. These imposed limitations may produce an initial sinogram with negative ray weights, a condition that is physically unrealizable. It has been determined however that iterative correction of the current dose map based on a calculation of the actual dose with negative ray weights truncated to zero can be used to produce a sinogram that converges to the desired dose.

The foregoing and other objects and advantages of the invention will appear from the following description. In the description, reference is made to the accompanying drawings which form a part hereof and in which there is shown by way of illustration several preferred embodiments of the invention. Such embodiments do not necessarily represent the full scope of the invention, however, and reference must be made therefore to the claims herein for interpreting the scope of the invention.

DETAILED DESCRIPTION OF THE PREFERRED EMBODIMENT

Figure 1:
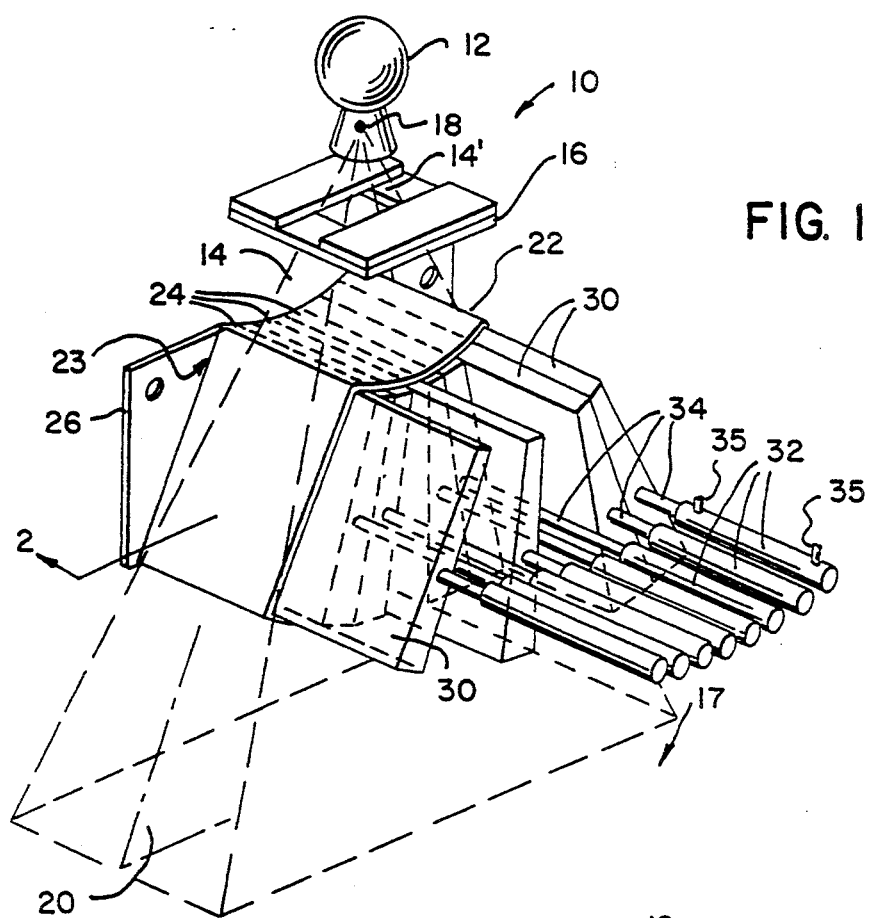
FIG. 1 is a perspective view of the compensator assembly used in a radiotherapy machine useful for practicing the present invention, showing the compensator leaves and their associated actuators.

Referring to FIG. 1, a radiation therapy unit 10 suitable for use with the present invention includes a radiation source 12 producing a generally conical radiation beam 14' emanating from a focal spot 18 and directed towards a patient 17 (not shown in FIG. 1). The conical beam 14' is collimated by a radiation opaque mask 16 constructed of a set of rectangular collimator blades to form a generally planar fan beam 14 centered about a fan beam plane 20.

I. The Compensator

A compensator 22 is centered in the fan beam 14 and about the fan beam plane 20, prior to the radiation being received by the patient 17, and includes a plurality of adjacent trapezoidal leaves 30 which together form an arc of constant radius about the focal spot 18. The leaves 30 are held in sleeves 24. The sleeves 24 are constructed of radio translucent materials and attached at their inner ends 23 to a mounting plate 26 which is fixed relative to the focal spot 18. The mounting plate 26 is constructed of a sturdy, radiopaque material and is positioned just outside the fan beam 14 to prevent interference with the fan beam 14.

Figure 2:
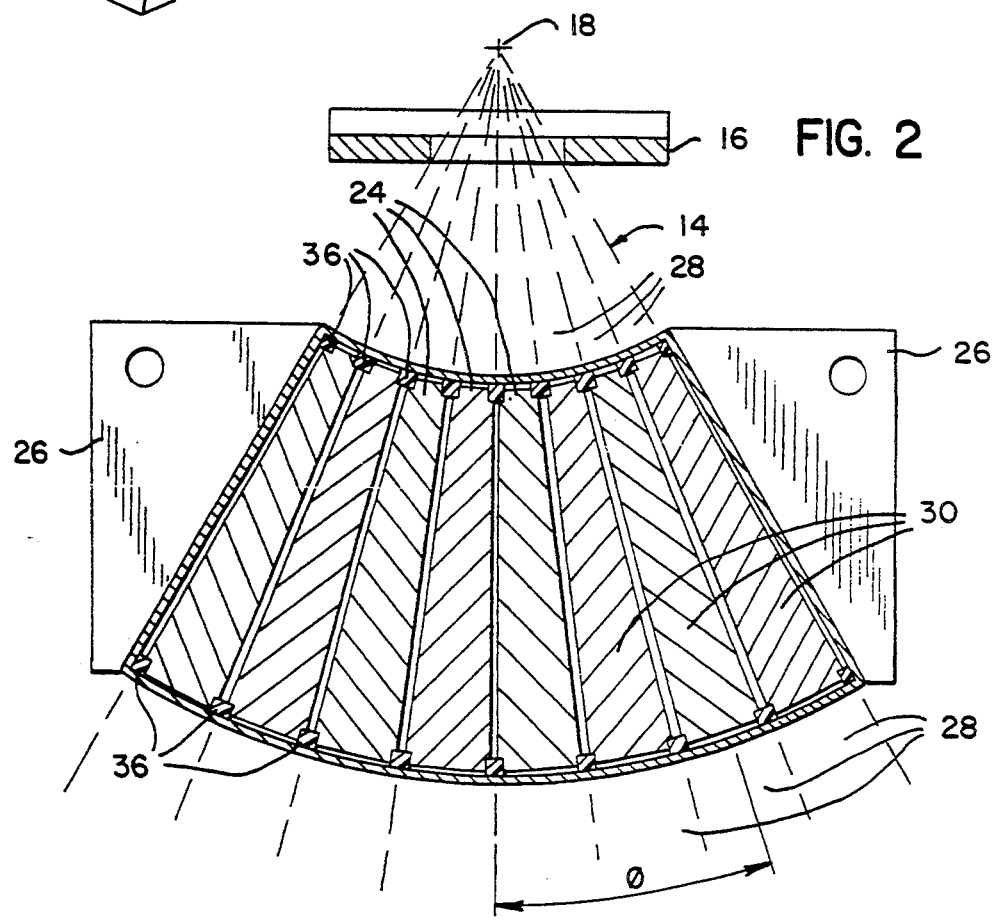
FIG. 2 is a cross-section of the compensator assembly of FIG. 1 along line 2—2 showing the trapezoidal aspect of each compensator leaf, for a fan beam of radiation, and the guide rails for supporting the compensator leaves when they move.

Preferably, the leaves 30 of the compensator 22 subtend the entire fan beam 14 to divide the fan beam 14 into a set of adjacent slab-like rays 28 at offset angles $\phi$. Referring also to FIG. 2, each sleeve 24 is open at its outer end 27 to receive, by sliding, a comparably sized trapezoidal leaf 30 constructed of a dense, radiopaque material such as lead, tungsten, cerium, tantalum or a related alloy.

Each leaf 30 may slide completely within its corresponding sleeve 24 to block the ray 28 associated with that sleeve 24. When the leaf 30 blocks its corresponding ray 28, it is referred to as being in a "closed state". The sleeves 24 are of ample length to permit each leaf 30 to slide out of the path of the fan beam 14, so as to leave its corresponding ray 28 completely unobstructed, and yet to still be guided by the sleeve 24. In this non-blocking position, a leaf is referred to as being in the "open state".

Each leaf 30 may be moved rapidly between its open and closed states by means of a corresponding actuator connected to the leaf 30 by a flexible link 34. The actuators 32 have internal pistons (not shown) that may be moved at high velocity between the ends of the actuators 32 by means of pressurized air coupled to the actuators 32 through supply hoses 35. The supply hoses 35 are fed by a compensator control (not shown in FIGS. 1 or 2) to be described below. The actuators 32 are capable of applying high forces to the leaves 30 to move them rapidly and independently between the open and closed states.

Figure 3:
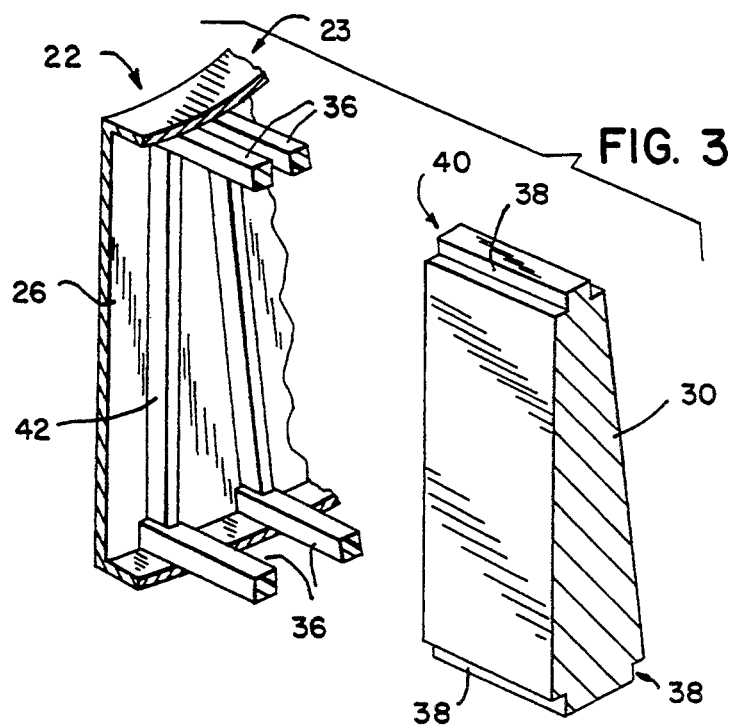
FIG. 3 is a cutaway perspective view of a set of guide rails and one leaf of FIG. 2 showing a collar for supporting the leaf in its fully closed position.

Referring now to FIGS. 2 and 3, the leaves 30 are supported and guided within the sleeves 24 by guide rails 36 fitted into notches 38 cut along the edges of the leaves 30. The notches 38 allow the guide rails 36 to slidably retain the leaves 30 within the sleeves 24 during motion between the open and closed states.

In the closed state, the inner end 40 of each leaf 30 is captured by a rigid collar 42 attached to the mounting plate, which aligns the leaf 30, more accurately than may be done by the guide rails 36, with the mounting plate 26 and hence with the fan beam 14. Whereas the guide rails 36, which are ideally radio translucent, are relatively insubstantial, in contrast, the collar 42, positioned outside the fan beam 14 on the mounting plate 26, need not be radio-translucent and hence is more substantial in construction A collar (not shown) similar to cellar 42, supports each leaf 30 when it is fully in the open state. Because the leaves 30 spend most of their time fully in the open or closed states, they are, at most times, firmly located by a supporting collar 42.

II. Radiation Therapy Hardware

Figure 4:
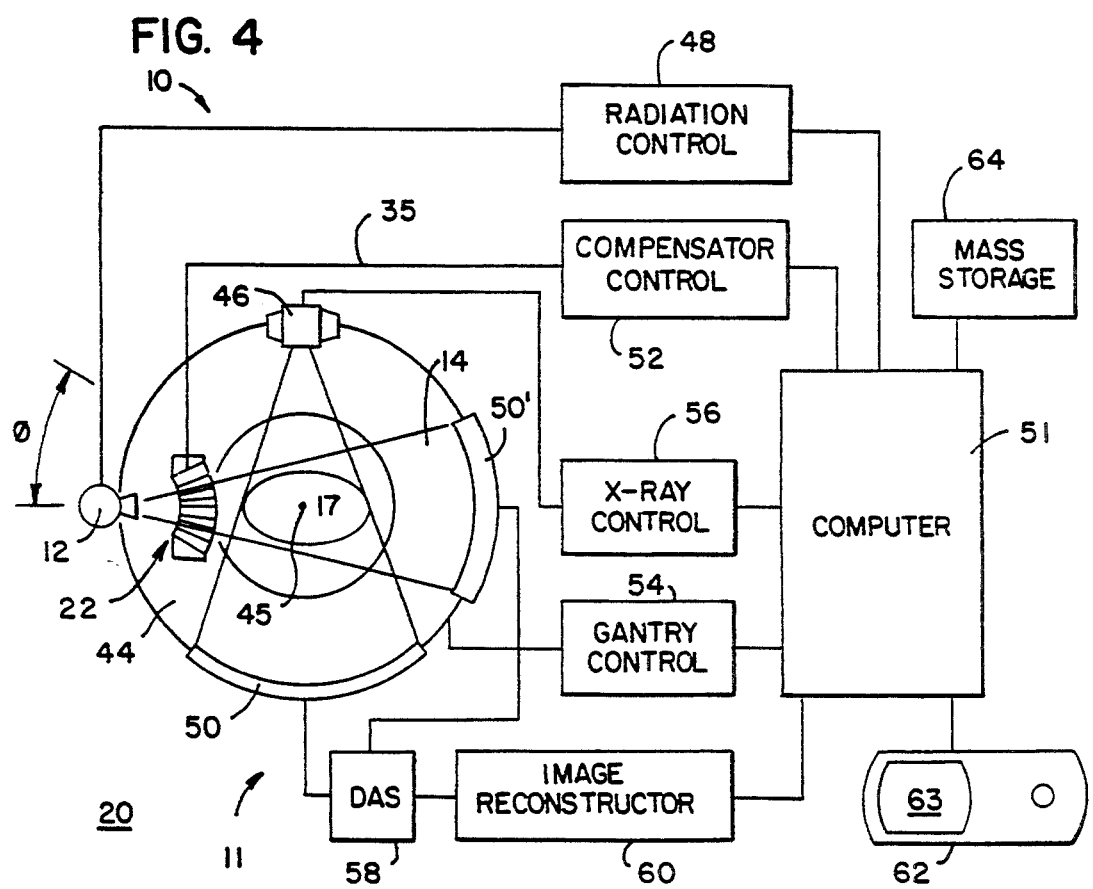
FIG. 4 is a block diagram showing the elements of a radiation therapy apparatus incorporating a conventional CT scanner and the compensator and including a computer suitable for controlling that compensator.

Referring now to FIG. 4, the radiation source 12 is mounted on a gantry 44, the latter rotating within the fan beam plane 20 about a center of rotation 45 in the patient 17 so that the fan beam 14 may irradiate a slice of the patient 17 from a variety of gantry angles $\phi$.

The radiation source 12 is controlled by a radiation control module 48 which turns the radiation beam 14 on or off under the control of a computer 51.

A compensator control module 52 provides a source of compressed air and valves to gate that air through supply hoses 35 to control, separately, the actuators 32 to move each of the leaves 30 in and out of its corresponding sleeve 24 and ray 28 (see also FIG. 1). The compensator control module 52 also connects with computer 51 to allow program control of the compensator 22 to be described.

A tomographic imaging system 11 employing an x-ray source 46 and an opposed detector array 50 may be advantageously mounted on the same gantry 44 as the radiation source 12 to produce a tomographic or slice image of the irradiated slice of the patient 17 prior to radiation therapy for planning purposes. Alternatively, such tomographic imaging may be performed on a separate machine and the slices aligned according to fiducial points on the patient 17.

A gantry control module 54 provides the signals necessary to rotate the gantry 44 and hence to change the position of the radiation source 12 and the angle $\phi$ of the fan beam 14 for the radiation therapy, as well as for the computed tomography x-ray source 46 and detector array 50 also attached to gantry 44. Gantry control module 54 connects with computer 51 so that the gantry may be rotated under computer control and also to provide the computer 51 with a signal indicating the gantry angle $\phi$ to assist in that control.

Control modules for the tomographic imaging system 11 include: x-ray control module 56 for turning on and off the x-ray source 46, and data acquisition system 58 for receiving data from the detector array 50 in order to construct a tomographic image. It will be understood to one of ordinary skill in the art that a detector array 50' may also be placed to receive radiation from the radiation source 12 through the patient 17 to assist in verification of the treatment, An image reconstructor 60 typically comprising a high speed array processor or the like receives the data from the data acquisition system 58 in order to assist in "reconstructing" a tomographic image from such data according to methods well known in the art, The image reconstructor 60 also communicates with computer 51 to assist in high speed computations used in the present invention as will be described below. The tomographic image allows verification of the patient setup just prior to radiation therapy treatment.

A terminal 62 comprising a keyboard and display unit 63 allows an operator to input programs and data to the computer 51 and to control the radiation therapy unit 10 and tomographic imaging equipment 11 and to display tomographic images produced by the image reconstructor 60 on the display 63. A mass storage system 64, being either a magnetic disk unit or tape drive, allows the storage of data collected by the tomographic imaging system 11 for later use.

Computer programs for operating the radiation therapy unit 10 will generally be stored in mass storage unit 64 and loaded into the internal memory of the computer 51 for rapid processing during use of the unit 10.

During operation of the radiation therapy unit 10, the compensator control module 52 receives from the computer 51 a fluence profile for each gantry angle. The fluence profile describes the intensity or fluence of each ray 28 of the fan beam 14 from the radiation source 12 that is desired for that gantry angle $\phi$ at a given position of the patient support table (not shown) as translated through the fan beam 14. Together, the fluence profiles for each gantry angle make up a treatment sinogram for a particular position of the patient table.

The compensator control module 52 moves the leaves 30 of the compensator 22 rapidly between their open and closed states to either fully attenuate or provides no attenuation to each ray 28. Gradations in the fluence of each ray, as needed for each fluence profile, are obtained by adjusting the relative duration during which each leaf 30 is in the closed position compared to the relative duration during which each leaf 30 is in the open position, for each gantry angle. The ratio between the closed and open states or the "duty cycle" for each leaf 30 affects the total energy passed by a given leaf 30 at each gantry angle and thus controls the average fluence of each ray 28. The ability to control the average fluence at each gantry angle permits accurate control of the dose provided by the fan beam 14 through the irradiated volume of the patient 17 by therapy planning methods to be described below.

The fluence profiles of the treatment sinogram are determined by therapy planning software (described below) and stored in the computer 51.

III. Therapy Planning Software

In a first embodiment, the generation of a treatment sinogram needed to obtain the full benefits of the above described compensator is performed by specially developed software running on the computer 51 and reconstructor 60. Although the treatment planning is performed in software, it will be recognized that the planning may also be implemented in discrete electronic circuitry dedicated to this operation and that such dedicated circuitry may be employed to provide even greater speed to this process. Finally, in a second embodiment, certain critical steps of the process may be performed on a special electrostatic computer to be described.

Figure 5:
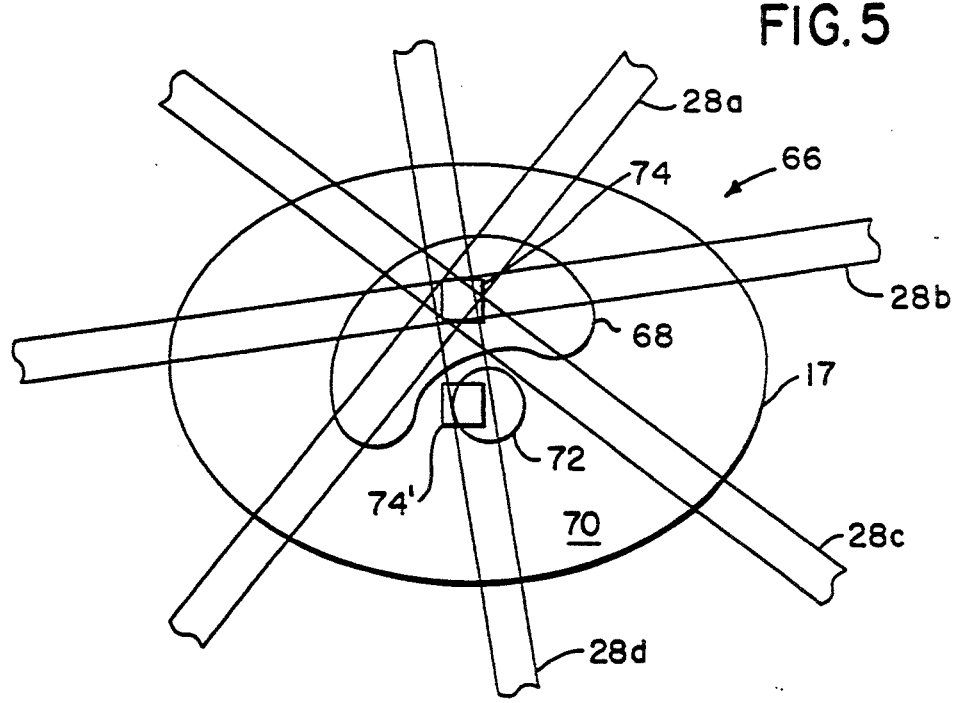
FIG. 5 is a simplified elevational view of a cross section of the patient showing a tumor and an adjacent radiation sensitive organ with multiple radiation beams converging at one voxel within the tumor.
Figure 7:
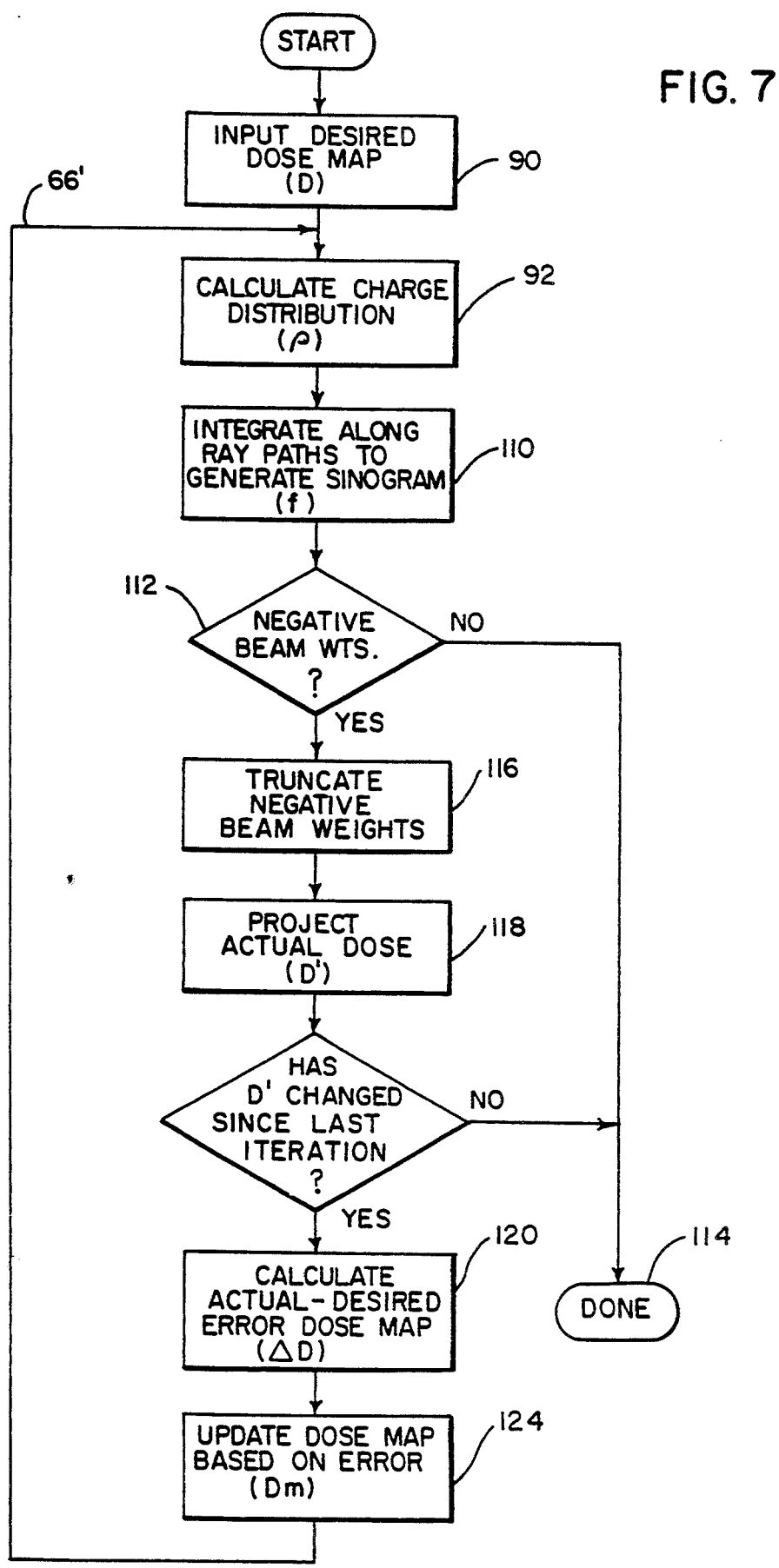
FIG. 7 is a flow chart showing the steps of the present invention for determining ray weights for the rays controlled by the collimator of FIGS. 1-3 at different gantry angles.

Referring to FIGS. 5 and 7, the generation of the desired treatment sinogram to control compensator 22 begins with the definition of a desired dose map 66. The dose map is a set of dose values identified to spatial coordinates or zones within the slice of the patient 17 to be irradiated. A typical desired dose map 66 assigns a relatively high radiation dose, within a dose constraint, to an area of tumorous tissue 68 and a second lower radiation dose to an area 72 including a radiation sensitive organ or the like.

The desired dose map 66 may be most easily entered by displaying the tomographic view of the slice of patient 17 on the display 63 of the terminal 62 (such as would appear similar to FIG. 5) and manually tracing around the tumorous area 68 and sensitive area 72 using a track-ball or similar input device as is well understood in the art. Standard area-filling computer programs may be used to transfer a predetermined uniform dose value to each traced region to the appropriate element in the array of memory representing the desired dose map 66.

The desired dose map 66 is stored within the memory of computer 51 as an array of elements, each element holding one numerical value and having a spatial coordinate corresponding to a position within a slice of the patient 17 to be treated.

Figure 6:
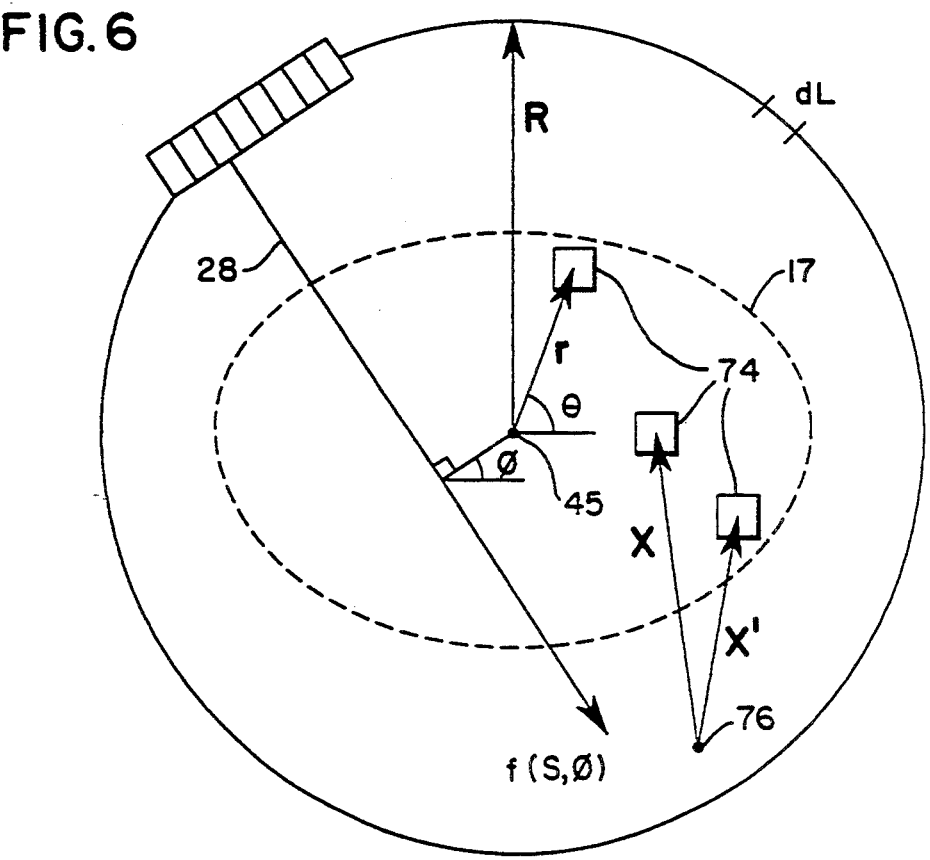
FIG. 6 is a geometric diagram showing the various spatial variables relevant to the calculation of the ray weights.

Each element of the dose map 66 defines the dose desired at each of the plurality of volume elements 74 ("voxels") within a slice of the patient 17. Referring to FIG. 6, each voxel 74 of the patient 17 may be identified by a vector x defined from a given reference point 76. The dose desired at each voxel 74 is D(x). The inputting of the desired dose map as described above is indicated by process block 90 and produces the array in memory $D_m(x)$.

Typically the dose at any given voxel 74 within the patient 17 will result from the combined effect of a number of different rays 28(a) through 28(d) produced at different gantry angles $\phi$. Nevertheless, the contribution to the dose at any voxel 74 from each ray 28 will not, in general, be equal. This is because each ray 28 necessarily sweeps out a continuous volume along its path that intersects other voxels 74 that may have different assigned doses. For example, ray 28(d) irradiating voxel 74 within tumor 68 also sweeps through voxel 74' in radiation sensitive organ 72. Thus, the dose to voxel 74 will preferentially be provided by rays other than 28(d). The measure of the relative strength of each ray will be generally termed the "ray weight".

The allocation of dose contribution among different rays 28, that is, the determination of ray weights, is an extremely complex problem. The present invention recognizes that one solution to this problem is that of modeling the desired dose map as the potential energy on a conductive plate. This recognition permits the use of many well-developed techniques previously used for solving electrostatic problems.

As will be described, once a charge distribution that would produce a potential field equal to the desired dose map 66 is determined, the ray weights for any given ray 28 may be simply determined by summing the charges along the path of that ray 28.

Referring now to FIG. 7, once the desired dose map 66 has been determined at process block 90, it is used to calculate a charge distribution in a volume corresponding to the treatment slice, as indicated at process block 92. The particular charge distribution is that which would produce a potential energy field equal to the input dose map 66.

Any stationary electrical charge, such as an electron, produces about it an electrostatic field. That field is generally a measure of the force exerted on a test charge within the region of the stationary electrical charge and is proportional to the inverse of the separation distance squared according to Coulomb's law.

The electrostatic field provides the test charge with a well defined potential energy proportional to simply the inverse of the separation distance. For a plurality of charges at positions x', the potential energy at a given position x is as follows:

$$P(x) = \int \frac{\rho(x')}{|x - x'|} d^2x' \quad (1)$$

where P(x) is the potential at spatial coordinate x,
$\rho(x')$ is the charge distribution at other spatial coordinates x', and
$|x - x'|$ is the distance between the two coordinates x and x'.

The calculation of charge distribution as indicated by process block 92 therefore requires simply determining a charge distribution $\rho(x)$ such that $P(x) = D_m(x)$. That is:

$$D_m(x) = \int \frac{\rho(x')}{|x - x'|} d^2x' \quad (2)$$

In a first method of calculating the charge distribution of process block 92, the electrostatic analogy is exploited in a special purpose electrostatic computer 91.

Figure 8:
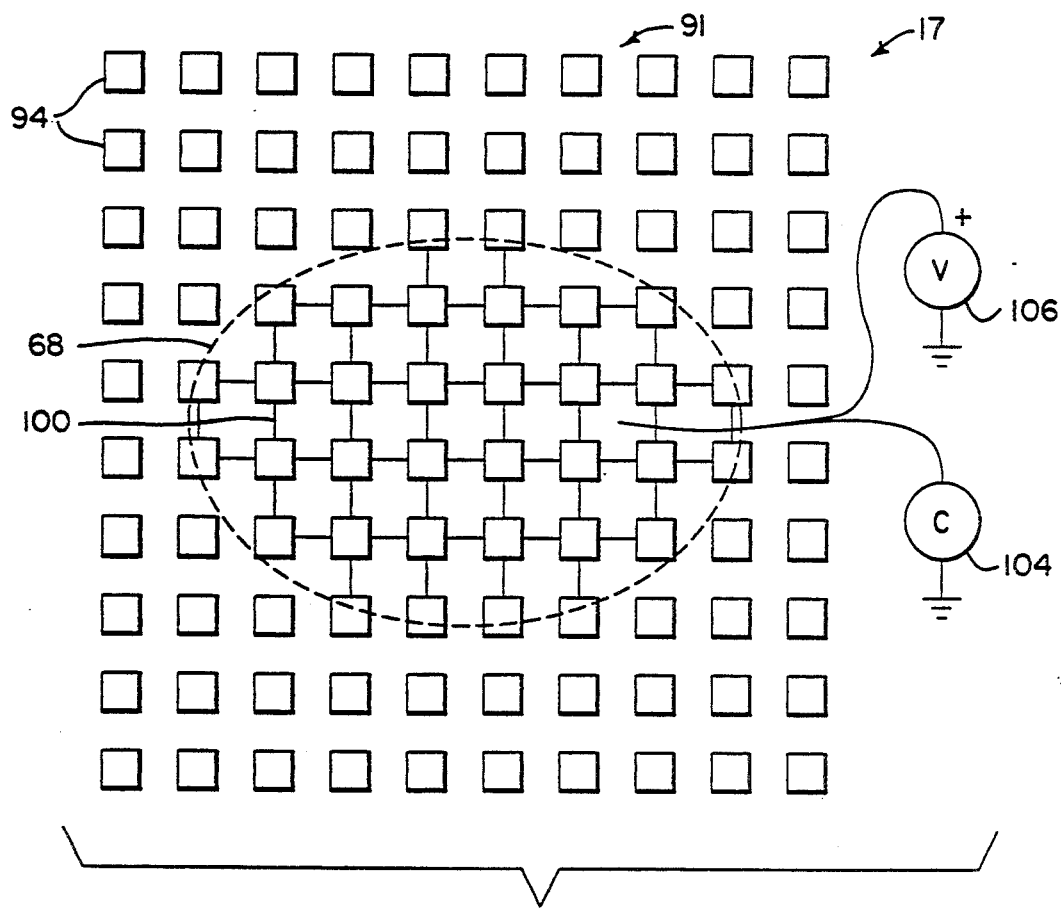
FIG. 8 is a schematic representation of a high speed electrostatic computer useful for determining a charge distribution in a tumor shaped area as simulated by a number of conducting elements.
Figure 9:
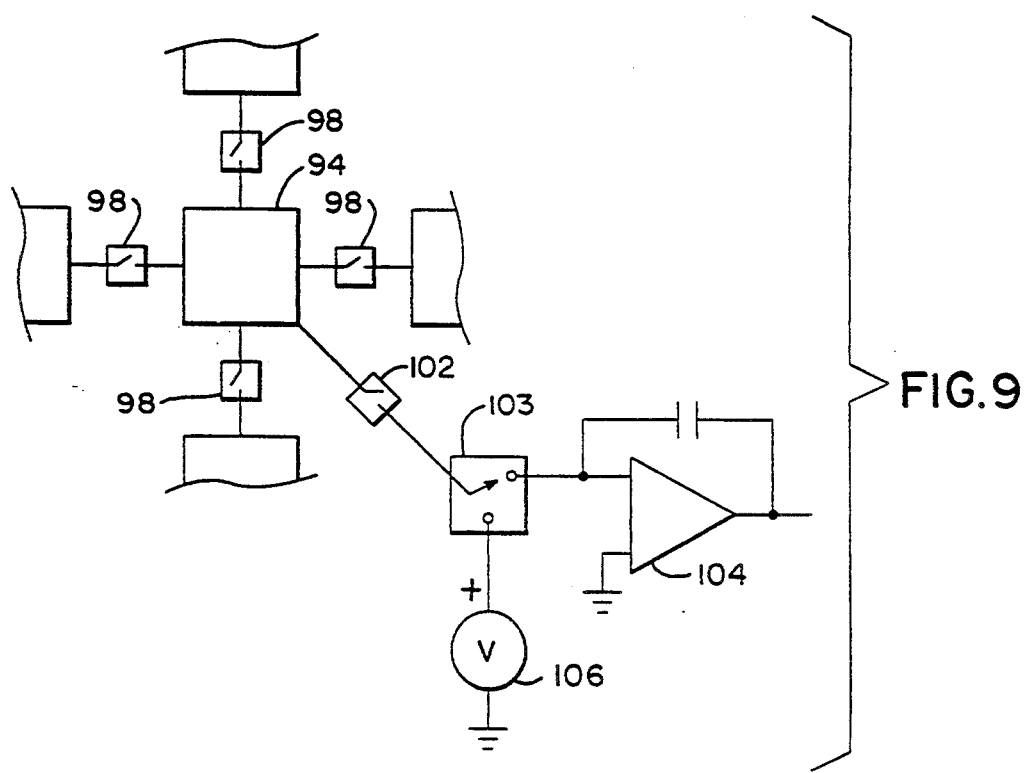
FIG. 9 is a detailed schematic of one such conductive element and its interconnection by a solid state switch to adjacent connective elements or to a charge amplifier or a voltage source.

Referring to FIGS. 8 and 9 in this electrostatic computer 91, the slice of the patient 17 is represented by a planar array of conductive elements 94 arranged in rectilinear columns and rows. Each conductive element 94 may be a square copper plate. Each conductive element 94 is interconnected along rows and columns, to its neighboring conductive elements 94, by four solid state switches 98 which may be closed to form a conductive link 100 between any two adjacent conductive elements 94 or opened to electrically isolate a conductive element 94 from its neighbors. Thus, when all solid state switches 98 are closed, the conductive elements 94 operate as a single conductive sheet.

Each conductive element is also connected via a solid state switch 102 to a charge amplifier 104 which may measure the charge on any isolated conductive element 94 or alternatively to a voltage source 106 as determined by switch 103.

The electrostatic computer 91 receives the dose map 66 and calculates the charge distribution as indicated by process block 92 by performing the following steps.

First, all the conductive elements 94 are connected together and grounded to remove any accumulated charge.

Second, the conductive elements 94 within a zone to receive a uniform dose value, such as the zone of tumor 68, are interconnected with links 100 by closing the necessary solid state switches 98. The interconnected elements 94 then form a conductive sheet having a perimeter matching that of the tumor 68 within the slice of the patient. The voltage source 106 is then connected to one of the interconnected conductive elements 94 and charge is allowed to flow into the interconnected elements 94 until its voltage potential of the elements 94 reaches the level corresponding to the desired dose of dose map 66. Because the conductive elements 94 form a single conductive sheet, the potential of each of the conductive elements 94 will be equal and only uniform doses within a given area may be modeled in this manner. This is not unduly restrictive however since typically a uniform dose will be desired over the entire area of the tumor within a slice. Further, if desired, sub zones may be used to approximate non-uniform dose distributions.

Once the desired potential is reached on the interconnected conductive elements 94, the charges will have migrated to various positions on the interconnected elements 94 as required to create a uniform potential field over those interconnected elements 94. At this time, in the third step, the interconnections 100 are broken by opening any closed solid state switches 98 and each conductive element 94 is isolated. Sequentially, each conductive element 94 is connected through solid state switch 102 to a charge amplifier 104 which produces an output voltage equal to the charge on that element 94. These output voltages are read through an analog to digital converter (not shown) to generate a matrix within computer 51 indicating the charge distribution $\rho(x)$.

An alternative method of calculating charge distribution for process block 92 is the modeling of the distribution of charges in computer 51. In this case, the calculation of the charge distribution is determined by sequential numerical methods.

A first approach uses Laplace's differential equation with the appropriate boundary conditions as determined by the outline of the various zones 68 or 72 defining the tumor or sensitive organ. Laplace's equation is:

$$\nabla^2 \Phi(x) = 0 \qquad (3)$$

where $\Phi$ is the electrostatic potential energy which must be set equal to the dose. Accordingly, the corresponding equation for the dose distribution is:

$$\nabla^2 D_m(x) = 0 \qquad (4)$$

The solution to Laplace's equation can be obtained numerically. Solution techniques are described by W. H. Press, B. P. Flannery, S. A. Teukolsky, and W. T. Vetterling, Numerical Recipes. (Cambridge University Press, 1986).

The solution of equation (4) primarily determines the fall-off of dose outside the region of the tumor. Once this potential energy distribution outside the tumor is obtained, the corresponding charge distribution $\rho(x)$ is given by Poisson's equation:

$$\nabla^2 \Phi(x) = -4\pi \rho(x) \qquad (5)$$

where the charge distribution is confined to a single plane, as is the case here. If the desired dose distribution is uniform, then the electric field at the surface of the plate is normal to the plate and the charge distribution can be derived using the simplified relation:

$$\rho(x) = -\frac{1}{4\pi |E|} = -\frac{1}{4\pi} \frac{\partial \Phi}{\partial z} \qquad (6)$$

where E is the electric field and z is the Cartesian coordinate normal to the plate. Note, that generally, with this technique, the dose need not be uniform throughout the area of any given zone.

In a third approach, the problem of determining the charge distribution may be solved numerically by discretizing equation (1). This method will be referred to as the Collocation Method. In this case, equation (1) becomes:

$$P(x_j) = \sum_{i=1}^{n} \frac{\rho(x_i)}{|x_j - x_i|} \Delta v \qquad (7)$$

where $\Delta v$ is the area of each voxel $x_1$.

This results in n linear equations which equate the dose at some voxel $x_j$ to a linear sum of charges, weighted by 1/r factors at the n discretized points. This system of equations can be solved using standard methods of linear algebra well known to those of ordinary skill in the art.

One complication to this approach is determining the effect of a given charge on itself as will occur when j=i and the denominator of equation (7) goes to zero. One approach to this problem is treated in *Integral Equation Methods in Potential Theory and Elastostatics* by M. A. Jaswon and G. T. Symm published by Academic Press, London 1977 and hereby incorporated by reference.

Referring to FIG. 7, after the charge distribution is determined by one of the above methods, the ray weights are determined according to process block 110. At process block 110 the charges defined by the charge distribution $\rho(x)$ are integrated (totaled) along the ray paths to generate the treatment sinogram.

Referring to FIG. 6, for a given ray 28 defined by an angle $\phi$ with respect to a horizontal x axis through the patient 17 and within the gantry plane and by a distance s of the ray's closest approach to the center of rotation 45, the fluence of that ray 28, f(s,$\phi$), is as follows:

$$f(s,\phi) = \int \frac{dq\rho(x)}{q} \qquad (8)$$

where:

f(s,φ) is the fluence for any given ray;

q is a distance variable along the ray used as the variable of integration.

These three steps of process block 90, 92 and 110 thus provide all the information necessary to generate a treatment sinogram for an arbitrary number of rays.

For a fan beam system where the rays of radiation 28 diverge about points along the radius of the radiation source about the origin 45, the individual rays of the fan beams at various gantry angles may be rebinned to sets of parallel rays to simplify the integration process.

For the simple case where the dose map 66 comprises a single zone 68 with a positive dose which does not spatially vary too quickly then the sinogram of ray weights at different gantry angles φ will include only non-negative ray weightings. Thus, after process 110 there will be no negative ray weights in the sinogram and, at decision block 112, the program will exit at exit point 114 having produced the necessary treatment sinogram.

For multiple zone dose maps 66, or those having concave zones or radiation sensitive zones 72 in proximity with the tumor zone 68, the steps of process blocks 90, 92 and 110 will often yield a sinogram with negative ray weights. Negative ray weights represent rays of radiation that do not impart dose as they pass through the patient 17 but absorb dose. Such negative ray weights are physically unrealizable. Accordingly, when negative ray weights are produced, an iterative procedure is used to eliminate the negative ray weights yet to still approximate the desired dose map 66.

At process block 116, the ray weights of the sinogram are reviewed and negative ray weights are replaced by ray weights of zero, the minimum realizable ray weight, to produce a truncated sinogram.

This truncated sinogram is used to determine an actual dose that would be received by the patient using the ray weightings of the truncated sinogram. The actual dose $D'(r,\phi)$ at each voxel 74, defined in standard polar coordinates as shown in FIG. 6, from all the rays 28 converging at each voxel 74, is:

$$D'(r,\theta) = \int_0^{2\pi} d\phi f[r\sin(\phi - \theta), \phi] \quad (9)$$

Equation (9) is simply the superposition of the dose contributed by each ray 28 intersecting a given voxel 74 to sum their contributions as indicated by process block 118.

Typically, after the truncation of the ray weights of process block 116, the actual dose, $D'$, produced by process block 118 will differ from the desired dose, $D$, originally input at process block 90. Accordingly, an error dose map, $\Delta D$, is calculated at process block 120 in which, at each voxel 74, the value of the desired dose, $D$, is subtracted from the actual dose, $D'$, as determined by process block 118. It will be expected that the actual dose, $D'$, will usually be higher than the desired dose, $D$, because negatively weighted rays have been truncated.

Ordinarily, the dose map will be updated at each iteration. The method will be considered to have converged when further iterations show no changes in the resulting actual dose. This is an indication that the best possible beam distribution has been found.

Typically, the error dose map, $\Delta D$, will not be acceptable at the initial iteration and the program will branch to process block 124 and the dose map, $D_m$, input to the charge distribution calculator of process block 92 will be modified. In the simplest embodiment, the new dose map, termed the "current dose map" will be equal to the error dose map times a constant r, ($r \times \Delta D$), subtracted from the last dose map provided to process block 92. For the first iteration, the error dose map, $\Delta D$, is subtracted from the desired dose map, $D$, while preserving the desired dose map, $D_m$, for future iterations. The modified desired dose map is termed the current dose map 66' and is again provided to the process block 92 for a new charge distribution to be calculated as indicated by a loop of the program from process block 124 back to process block 92.

For all iterations after the first iteration, it is the current dose map 66' ($D_m$) that will be corrected by the error dose map, $\Delta D$.

The inventors believe that the adjustment of the current dose map ($D_m$) provides an iterative solution that converges rapidly to the best treatment sinogram.

EXAMPLE I

In a computer simulation, a grid was formed of nine tumor target voxels with $-1 \leq x \leq 1$ and $-1 \leq y \leq 1$. An organ voxel to be avoided had coordinates $x=3$, $y=0$. Beams were incident with φ values $\pi/2$, $7/12\pi$, $11/12\pi$; from each φ value there were seven rays emerging, each having an angular width of 0.174 radians (about 10°). The iterative method described converged to yield the best possible set of beam weights in 10 iterations. The solution yields dose uniformity in the tumor target to within ±2%, with only 6% maximum dose delivered to the organ.

The above description has been that of a preferred embodiment of the present invention. It will occur to those who practice the art that many modifications may be made without departing from the spirit and scope of the invention. For example, the dose within any given zone need not be uniform but may be varied as research indicates the optimum dose distribution within a tumor. Clearly the method for planning radiation therapy is not limited to a particular radiation source but may be used with any radiation source which may be decomposed into separate radiation rays. In order to apprise the public of the various embodiments that may fall within the scope of the invention, the following claims are made:

We claim:

1. In a radiation therapy device having a radiation source for producing a radiation beam directed toward a volume of a patient at a plurality of gantry angles within a gantry plane, the beam including a plurality of rays dispersed within the gantry plane, each ray having an independently adjustable fluence, one ray following a path at one gantry angle, a therapy planning apparatus to determine the fluence of each ray comprising:

an electronic computer including the following means:

a means for receiving a desired dose map of desired radiation dose along a slice through the volume of the patient;

a charge calculator means for calculating a distribution of electrical charges within the slice that would produce a potential energy field corresponding to the desired dose map; and an integration means for integrating the charges of the distribution that lie along the path to determine the fluence of the ray at the gantry angle.

2. The radiation therapy device of claim 1 wherein the charge calculator is a conductive sheet formed from a plurality of connectable conductive elements first joined together to receive a charge, in at least one dose region, and second electrically isolated from one another to measure the charge on each isolated element.

3. The radiation therapy device of claim 1 wherein the charge calculator is a digital computer receiving the dose map as an array of numerical values and modeling the charge distribution according to the following relation:

$$D(x) = \int \frac{\rho(x')}{|x - x'|} d^2x'$$

where:
$D(x)$ is the desired dose at spatial coordinate x,
$\rho(x')$ is the charge distribution at other spatial coordinates x', and
$|x-x'|$ is the distance between the two coordinates x and x'.

4. The radiation therapy device of claim 1 wherein the integration means determines the fluence of the ray along the path according to the following relation:

$$f(s,\phi) = \int \frac{dq\rho(x,y)}{q}$$

where:
$f(s,\phi)$ is the fluence for any given ray;
q is a distance variable along the ray used as the variable of integration; and
$\rho(x,y)$ is the charge distribution over the slice.

5. In a radiation therapy device having a radiation source for producing a radiation beam directed toward a volume of a patient at a plurality of gantry angles within a gantry plane, the beam including a plurality of rays dispersed within the gantry plane, each ray having an independently adjustable fluence, one ray following a path at a gantry angle, a therapy planning apparatus comprising:
an electronic computer including the following means:
a means for receiving a desired dose map having, first, a tumor zone to receive at least a treatment threshold of radiation and, second, an organ zone to receive no more than a tolerance threshold of radiation, the two zones lying along a slice through the volume of the patient and for producing a current dose map equal to the desired dose map;
a charge calculator means receiving the current dose map for calculating a distribution of electrical charges within the tumor zone and organ zone that would produce a potential energy field corresponding to the dose map in each zone; and
an integration means for integrating the charges of the distribution that lie along the path to determine the fluence of the ray at the gantry angle.

6. The radiation therapy device of claim 5 including in addition:
(a) means for repeating the integration of charges for the plurality of rays at the plurality of gantry angles to create a sinogram of fluence values;
(b) means for setting any negative fluence values in the sinogram to a predetermined non-negative value to create an adjusted sinogram;
(c) means for determining the actual dose that would be produced by rays having the fluence values of the adjusted sinogram to create an actual dose map;
(d) means for evaluating the difference between the actual dose map and the desired dose map to modify the current dose map;
wherein the current dose map may be repeatedly adjusted to produce an actual dose map that closely approximates the desired dose map without rays having negative fluence values.

7. The radiation therapy device of claim 6 wherein the current dose map is modified by subtracting the difference between the actual dose map and the desired dose map from the current dose map.

8. The radiation therapy device of claim 6 wherein the charge calculator determines the distribution of charge according to the following relation:

$$D(x) = \int \frac{\rho(x')}{|x - x'|} d^2x'$$

where:
$D(x)$ is the desired dose at spatial coordinate x,
$\rho(x')$ is the charge distribution at other spatial coordinates x', and
$|x-x'|$ is the distance between the two coordinates x and x'.

9. The radiation therapy device of claim 6 wherein the integration means determines the fluence of the ray along the path according to the following relation:

$$f(s,\phi) = \int \frac{dq\rho(x,y)}{q}$$

where:
$f(s,\phi)$ is the fluence for any given ray;
q is a distance variable along the ray used as the variable of integration; and
$\rho(x,y)$ is the charge distribution over the slice.

10. A method of radiation therapy planning for a radiation therapy device having a radiation source producing a radiation beam directed toward a slice of a patient at a plurality of gantry angles within a gantry plane, the beam including a plurality of rays dispersed within the gantry plane, each ray having an independently adjustable fluence, one ray following a path through the slice at a gantry angle, the method comprising the steps of:
(a) entering a desired dose map along a slice through the volume of the patient, as a set digital value in an electronic computer, the digital values representing dose of ionizing radiation needed to treat the patient;
(b) calculating a distribution of electrical charges within the slice that would produce a potential energy field corresponding to the desired dose map;
(c) integrating the charges of the distribution that lie along the path to determine the fluence of the ray at the gantry angle.

11. The method of claim 10 wherein step (b) calculates the distribution of charge according to the following relation:

$$D(x) = \int \frac{\rho(x')}{|x - x'|} d^2x'$$

where:

D(x) is the desired dose at spatial coordinate x,

ρ(x') is the charge distribution at other spatial coordinates x', and

|x−x'| is the distance between the two coordinates x and x'.

12. The method of claim 10 wherein step (c) determines the fluence of the ray along the path according to the following relation:

$$f(s,\phi) = \int \frac{dq\rho(x,y)}{q}$$

where:

f(s,φ) is the fluence for any given ray;

q is a distance variable along the ray used as the variable of integration; and

ρ(x,y) is the charge distribution over the slice.

13. A method of radiation therapy planning used on a radiation therapy device having a radiation source for producing a radiation beam directed toward a volume of a patient at a plurality of gantry angles within a gantry plane, the beam including a plurality of rays dispersed within the gantry plane, each ray having an independently adjustable fluence, one ray following a path at a gantry angle, the method comprising the steps of:

(a) defining a desired dose map having, first, a tumor zone to receive at least a treatment threshold of radiation and, second, an organ zone to receive no more than a tolerance threshold of radiation, the two zones lying along a slice through the volume of the patient and for producing a current dose map equal to the desired dose map;

(b) calculating a distribution of electrical charges within the tumor zone and organ zone that would produce a potential energy field corresponding to the current dose map in each zone; and (c) integrating the charges of the distribution that lie along the path to determine the fluence of the ray at the gantry angle.

14. The method of claim 13 including the steps of:

(d) repeating the integration of charges for the plurality of rays at the plurality of gantry angles to crate a sinogram of fluence values;

(e) setting any negative fluence values in the sinogram to a predetermined non-negative value to create an adjusted sinogram;

(f) determining the actual dose that would be produced by rays having the fluence values of the adjusted sinogram to create an actual-dose map;

(g) means for evaluating the difference between the actual dose map and the desired dose map to modify the current dose map;

(h) repeating steps (b) through (g) until further repetitions do not change the difference.

15. The radiation therapy device of claim 14 wherein step (b) determines the distribution of charge according to the following relation:

$$D(x) = \int \frac{\rho(x')}{|x - x'|} d^2x'$$

where:

D(x) is the desired dose at spatial coordinate x,

ρ(x') is the charge distribution at other spatial coordinates x', and

|x−x'| is the distance between the two coordinates x and x'.

16. The radiation therapy device of claim 14 wherein step (c) determines the fluence of the ray along the path according to the following relation:

$$f(s,\phi) = \int \frac{dq\rho(x,y)}{q}$$

where:

f(s,φ) is the fluence for any given ray;

q is a distance variable along the ray used as the variable of integration; and

ρ(x,y) is the charge distribution over the slice.

* * * * *